United States Patent [19]

Narushima et al.

[11] Patent Number: 4,725,443
[45] Date of Patent: Feb. 16, 1988

[54] MEAT TENDERIZATION WITH PROTEOLYTIC ENZYME-CONTAINING OIL

[75] Inventors: Noriyuki Narushima, Chiba; Yoshihiro Sekino, Kanagawa, both of Japan

[73] Assignee: Kibun Company Limited, Tokyo, Japan

[21] Appl. No.: 6,273

[22] Filed: Jan. 20, 1987

Related U.S. Application Data

[63] Continuation of Ser. No. 574,614, Jan. 27, 1984, abandoned.

[30] Foreign Application Priority Data

Feb. 17, 1983 [JP] Japan ................................. 58-023734
Feb. 17, 1983 [JP] Japan ................................. 58-023735

[51] Int. Cl.$^4$ ............................ A23L 1/31; C12N 9/50
[52] U.S. Cl. ........................................ 426/56; 426/63; 435/219
[58] Field of Search .................... 426/56, 63; 435/188, 435/219

[56] References Cited

U.S. PATENT DOCUMENTS

| | | | |
|---|---|---|---|
| 2,140,781 | 12/1938 | Allen | 426/56 |
| 2,321,623 | 6/1943 | Ramsbottom et al. | 426/56 |
| 2,825,654 | 3/1958 | Vaupel | 426/63 |
| 3,296,094 | 1/1967 | Czyle | 426/63 |

FOREIGN PATENT DOCUMENTS

| | | | |
|---|---|---|---|
| 1095093 | 12/1960 | Fed. Rep. of Germany | 426/56 |
| 900794 | 7/1962 | United Kingdom | 426/63 |

OTHER PUBLICATIONS

Woollen, A., Food Industries Manual, 20th ed., Chemical Publ. Co., Inc. X1-Y, 1970, pp. 190-193.

*Primary Examiner*—David M. Naff
*Attorney, Agent, or Firm*—Browdy and Neimark

[57] ABSTRACT

Beef, fish and fowl are tenderized, without oozing out flavoring substances, by contacting with oil and/or fat containing a proteolytic enzyme. Preferably, contacting is by soaking in a composition consisting of oil and proteolytic enzyme at 5°-10° C. for 24-48 hours.

1 Claim, No Drawings

MEAT TENDERIZATION WITH PROTEOLYTIC ENZYME-CONTAINING OIL

This application is a continuation of application Ser. No. 574,614, filed Jan. 27, 1984, now abandoned.

The present invention relates to a novel oil and/or fat composition.

More particularly, the present invention relates to an oil and/or fat composition which is used for softening or cooking meats.

Moreover, the present invention also relates to a method of treating meat with enzymes.

More particularly, the present invention relates to a method of producing tenderized meat-containing food which comprises softening meats and also improving the flavour thereof, and cooking them.

In general, when a cut of salmon or beef, especially frozen one, is cooked by heating, it is well known that the texture thereof tightens. Therefore, it has a very tough and unfavourable mouth feel when eating.

Hitherto, in order to tenderize beef and the like, it has been immersed in an aqueous solution of proteolytic enzyme.

When beef and the like is immersed in an aqueous solution containing proteolytic enzyme, however it results in only surface treatment due to poor permeability, or an extract oozes from meat into said aqueous solution of enzyme. Therefore this method suffers such a disadvantage that a good taste is spoiled.

The present inventors have pursued their studies in order to improve the permeability of proteolytic enzyme into meats, and as a result, completed the present invention.

In general, those skilled in the art would not consider containing a proteolytic enzyme in oil and/or fat, because of the problems of deactivation and/or poor dispersion of proteolytic enzyme within oil and/or fat. The inventors, however, have ventured upon this difficult problem and through testing, discovered unexpectedly that a proteolytic enzyme can be dissolved or dispersed in an oil and/or fat uniformly without causing any deactivation of enzyme according to the present invention.

As the oil and/or fat which is used in the present invention, such as vegetable oil, animal oil, or any other edible oil and/or fat can be all utilized. The oil and/or fat can be used either alone or in admixture therewith. Among them, such a vegetable oil that contains a large amount of unsaturated fatty acid which is liquid at a room temperature is particularly preferable. For example, there may be mentioned: lard, beef tallow, peanut oil, cocoanut oil, cotton seed oil, sunflower oil, palm kernel oil, rape oil, corn oil, soybean oil, safflower oil, rice oil, sesame oil or olive oil. These oils are respectively usable along or in combination therewith.

As the proteolytic enzyme which is used in the present invention, the proteolytic enzyme originating from animal source, plant source or microbial source can be all utilized, and as well all kinds of the proteolytic enzyme can be also utilized. As examples of proteolytic enzymes originating from animal source may be mentioned pepsin, trypsin and the like, and as examples thereof originating from plant source may be mentioned papain, bromelin and the like, and as examples thereof originating from microbial source may be mentioned bacterial protease, mould protease, basidiomycetous protease, actinomycetous protease and the like. In addition, the proteolytic enzyme are further classified into acid protease, neutral protease, alkali protease and the like, and all kinds of these enzymes can be effectively used in the present invention. In the present invention, the proteolytic enzyme purified to a high degree may be used, however, the crude enzyme which is commerically available is also suitable used.

A suitable amount of proteolytic enzyme is added to an oil and/or fat, and the upper limit thereof is preferably set at such an amount that the oil and/or fat is dissolved or dispersed therein uniformly. Proteolytic enzyme may be added adequately, and it is enough to add it in an amount of about 0.05 to 0.5% in order to prepare the oil and/or fat composition for tenderizing beef. However, in order to prepare the oil and/or fat composition which is diluted with oil and/or fat at the time of use, it is preferable to add the proteolytic enzyme in an amount of about 1 to 5%.

Mixing may be carried out at a room temperature, but in case of beef tallow or lardd which is solid at a room temperature, it is preferable to dissolve it by heating then add the proteolytic enzyme to thus dissolved fat and mix thoroughly.

It is enough to mix with simple agitation, and when mixing is carried out for 2 to 3 minutes with moderate agitation by using a mixer, the proteolytic enzyme is dissolved or dispersed uniformly to obtain an oil and/or fat composition without turbidness.

In addition, it may be also possible to emulsify the oil and/or fat composition of the present invention by adding a small amount of water or aqueous solution. As an aqueous solution, there can be adequately used, for example, soy sauce, vinegar, mixed liquid seasoning and the like. A great amount of water or aqueous solution may be used, however, the upper limit thereof is set as such an amount that the flavouring substances do not ooze out from meat, therefore the amount thereof is preferably about 1 to 10%. In order to maintain a good emulsification, an emulsifier such as sugar ester etc. may be added in a small amount.

The proteolytic enzyme contained in thus obtained oil and/or fat composition keeps the enzymatic activity, so that it can be used for a long time.

According to the present invention, the meat is treated with thus obtained oil and/or fat composition in such a manner that the meat is immersed in or added with this composition.

For example, with respect to beef or salmon meat etc. which has been tough due to freezing or will be tough due to cooking by heating, it is cut into slices of about 1 to 2 cm thick, then they are immersed in the oil and/or fat composition and they are allowed to stand for 48 hours at 5° to 10° C. Thus treated slices are roasted to be well tenderized. Moreover, in case of producing a hamburg steak, the oil and/or fat composition containing proteolytic enzyme has been added to minced meat in a small amount, and when a raw hamburg steak containing thus treated minced meat is cooked by heating, the grains of meat are kept in tenderized condition, and even if they are allowed to stand as they are, they do not become tough in a minute.

It is considered that since the oil and/or fat composition containing proteolytic enzyme has an excellent permeability to meat, the proteolytic enzyme permeates the meat all over, so that the whole meat is uniformly tenderized. In addition, as this oil and/or fat composition does not cause the flavouring substances and the like to be oozed out, it does not change the taste of food. Therefore, the added oil and/or fat composition can be allowed to be remained efficiently in the cooked food as it is without removing therefrom.

Some specific embodiments of the present invention will now be described in the following Examples.

EXAMPLE 1

20 g of koji mould protease (Trade name: Punchidase NP-2) was added to 10 kg of safflower oil, then the resulting mixture was agitated for 3 minutes to obtain a uniform oil composition.

EXAMPLE 2

10 g of papain was added to 10 kg of corn oil, then the resulting mixture was agitated for 2 minutes to obtain a uniform oil composition.

EXAMPLE 3

To the oil compostion obtained in the same manner as in Example 1, soy sauce was added in an amount of 5%, then the resultiing mixture was agitated for 2 minutes to obtain a uniform oil composition.

EXAMPLE 4

500 g of the oil composition obtained in the same manner in Example 1 was charged in a vessel, followed by the immersion of a sliced frozen side of cattle having a thickness of 1 cm, and then allowed to stand for 48 hours at 10° C. Thus treated sliced beef was panfried to obtain such a tenderized beef steak that it is impossible to be imagined that it was such one prepared by cooking a frozen beef.

EXAMPLE 9

500 g of the oil composition obtained in the same manner in Example 2 was charged in a vessel, followed by the immersion of a slice of salmon having a thickness of 1 cm, and then allowed to stand for 48 hours at 10° C. Thus treated sliced salmon was broiled in a gas fish-oven to obtain a tenderly broiled salmom slice.

EXAMPLE 6

100 g of the oil composition obtained in the same manner in Example 1 was added to 500 g of minced frozen beef, mixed therewith and the resulting mixture was allowed to stand for 24 hours at 10° C. Thus treated one was mixed with bread crumb, milk and panfried onion in a suitable amount, the resulting mixture was molded into a shape of hamburg steak, and it was cooked by heating.

Thus obtained hamburg steak was very tender in spite of using a frozen beef, and even if it was allowed to stand for a while, it did not become tough.

EXAMPLE 7

500 g of the oil composition obtained in the same manner in Example 1 was charged in a vessel, followed by the immersion of a sliced raw side of cattle having a thickness of 1 cm, and then allowed to stand for 48 hours at 10° C. Thus treated sliced beef was took out from the vessel, each one was wrapped respectively, then frozen and preserved at −30° C.

After three months preservation, thus frozen sliced beef was panfried to obtain such a tender beef steak that it is impossible to be imagined that it was such one prepared by cooking a frozen beef.

EXAMPLE 8

500 g of the oil composition obtained in the same manner in Example 1 was charged in a vessel, followed by the immersion of a sliced frozen side of cattle having a thickness of 1 cm, and then allowed to stand for 48 hours at 10° C. Thus treated sliced beef was took out from the vessel, each one was wrapped respectively, then frozen and preserved at −30° C.

After three months preservation, thus frozen sliced beef was panfried to obtain such a tender beef steak that it is impossible to be imagined that it was such one prepared by cooking a frozen beef.

What is claimed is:

1. A method for tenderizing meat, which comprises soaking one member selected from the group consisting of beef, fowl, and fish in a tenderizer consisting of an oil and 0.05%–5% of a proteolytic enzyme at 5°–10° C. for 24–48 hours.

* * * * *